(12) United States Patent
Worth (10) Patent No.: US 10,782,274 B2
(45) Date of Patent: *Sep. 22, 2020

(54) PORTABLE LONG TERM GAS DETECTING AND MONITORING APPARATUS

(71) Applicant: Acrulog Pty Ltd, Clontarf QLD (AU)

(72) Inventor: Brian Worth, Woody Point (AU)

(73) Assignee: Acrulog Pty Ltd, Clontarf QLD (AU)

( * ) Notice: Subject to any disclaimer, the term of this patent is extended or adjusted under 35 U.S.C. 154(b) by 264 days.

This patent is subject to a terminal disclaimer.

(21) Appl. No.: 15/969,777

(22) Filed: May 3, 2018

(65) Prior Publication Data

US 2018/0348183 A1 Dec. 6, 2018

(30) Foreign Application Priority Data

May 12, 2017 (AU) .................................. 2017901763

(51) Int. Cl.
*G01N 33/00* (2006.01)

(52) U.S. Cl.
CPC ..... *G01N 33/0032* (2013.01); *G01N 33/0006* (2013.01); *G01N 33/006* (2013.01); *G01N 33/007* (2013.01); *G01N 33/0008* (2013.01); *G01N 33/0031* (2013.01)

(58) Field of Classification Search
CPC .......... G01N 33/0006; G01N 33/0008; G01N 33/0031; G01N 33/0032; G01N 33/007; G01N 33/006

See application file for complete search history.

(56) References Cited

U.S. PATENT DOCUMENTS

| 10,557,838 | B2 * | 2/2020 | Worth | G01N 33/007 |
| 2011/0023581 | A1 * | 2/2011 | Chou | B01D 53/261 |
| | | | | 73/23.42 |
| 2011/0178722 | A1 * | 7/2011 | Roca | G01T 1/178 |
| | | | | 702/24 |

* cited by examiner

*Primary Examiner* — Paul M. West
(74) *Attorney, Agent, or Firm* — Michael W. Goltry; Robert A. Parsons; Parsons & Goltry, PLLC (57) ABSTRACT

A long term portable gas detecting and monitoring apparatus includes a case having a continuous sidewall including a first end closed by a first end cap, and a second end closed by a second end cap connected sealably and removably to the continuous sidewall. The continuous sidewall is triangular between the closed end and the open having three sides and three corners, two of the three sides being straight and equal in length, one of the three sides being rounded, and each of the three corners being rounded. A long term gas detection and monitoring unit mounted in the case includes gas, and temperature and humidity sensors in communication with an ambient atmosphere outside the case, a data processor operatively connected to the sensors, data storage, an information display viewable through the case, and a calibration unit for calibrating the gas sensor to a predetermined gas concentration measured by the gas sensors.

24 Claims, 5 Drawing Sheets

PORTABLE LONG TERM GAS DETECTING AND MONITORING APPARATUS

FIELD OF THE INVENTION

The present invention relates to apparatus and methods for long term detecting and monitoring gases in chosen environments, such as wastewater infrastructures and other hostile environments, over an extended period of time, with reduced rate of sensor decay and moister uptake.

BACKGROUND OF THE INVENTION

Gas detectors for detecting and/or monitoring harmful and/or offensive gases are widely used in industry, such as in industrial plants, refineries, pharmaceutical manufacturing facilities, fumigation facilities, paper pulp mills, aircraft and ship-building facilities, hazmat operations, waste-water treatment facilities, and other hostile environments. Prior art gas detectors are inherently restricted in their capabilities and effective life in harsh or hostile environments due to the poor conditions and/or levels of corrosive substances and/or humidity. Moreover, sensor leakages and data loss due to excessive humidity uptake and sensor drop off, commonly occur in prior art gas sensors designed for use in hostile, humid environments. Given these and other deficiencies the need for continual improvement is evident.

SUMMARY OF THE INVENTION

A long term portable gas detecting and monitoring apparatus includes; a long-term gas detection and monitoring unit mounted in a case. The case includes a continuous sidewall having opposed first and second ends. The first end is closed by a first end cap. The second end is closed by a second end cap. The first end cap is integral with, being inseparable from, the first end of the continuous sidewall. The second end cap is connected sealably and removably to the continuous sidewall. The continuous sidewall is triangular, having three sides and three corners, between the first end and the second end, two of the three sides being straight and equal in length, one of the three sides being rounded, and each of the three corners being rounded. The long term gas detection and monitoring apparatus includes; gas sensors in sealed fluid communication with an ambient atmosphere outside the case, a temperature and humidity sensor in sealed fluid communication with the ambient atmosphere outside the case, an inner temperature and humidity sensor in sealed fluid communication with the atmosphere inside the case, a data processor operatively connected to the gas sensors, the temperature and humidity sensor, and the inner temperature and humidity sensor, data storage and an information display operatively connected to the data processor, a calibration unit operatively connected to the data processor for calibrating the data processor to a predetermined gas concentration measured by the gas sensors, an externally operable switch for selectively connecting the data processor to the data storage to allow transfer of data from the data storage to the data processor, and a communication device operatively connected to at least one of the data processor and the data storage for enabling data transfer between an external destination and at least one of the data processor and the data storage. A power supply mounted in the case is operatively connected to power the long-term gas detecting and monitoring apparatus. An alternating plate to be controlled by the data processor via, a motor and control system, connected to the power supply. The gas sensors are mounted to the second end cap and are in sealed fluid communication via an alternating passage of the second end cap. The temperature and humidity sensor is mounted to the second end cap and is in sealed fluid communication via a second passage of the second end cap. The inner temperature and humidity sensor is mounted to the second end cap and is in sealed fluid communication with the inner volume. The information display confronts the rounded one of the three sides of the continuous sidewall. The rounded one of the three sides of the continuous sidewall is transparent to enable the viewing of the information display therethrough. There is a catch formed in the first end of the case from which the apparatus can be suspended. An internal humidity and temperature sensor monitors the inner volume temperature and humidity level. The communication device is a wireless communication device for enabling wireless data transfer between the external destination and at least one of the data processor and the data storage. The long-term gas detecting and monitoring apparatus further includes an inertial sensor sealed from the ambient atmosphere, and the data processor is operatively connected to the inertial sensor. The data process is for calculating at least one of, and preferably both, moisture uptake level and moisture uptake rate of the gas sensors, when the temperature and humidity sensors are sensing moisture of the ambient atmosphere outside the case and inner volume.

BRIEF DESCRIPTION OF THE DRAWINGS

Referring to the drawings.

DETAILED DESCRIPTION

Figure 1:
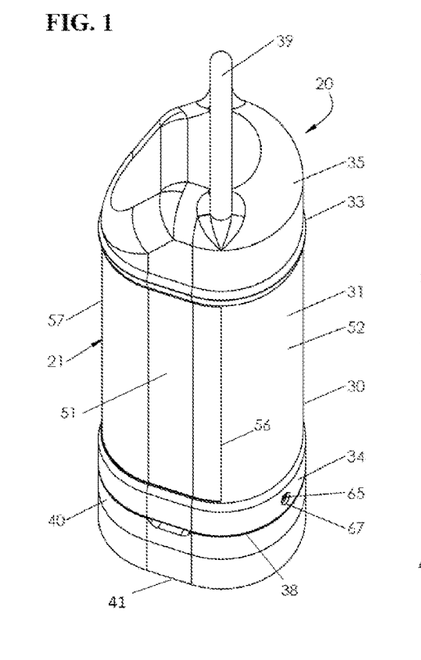
FIG. 1 is a top perspective view of a portable gas detecting and monitoring apparatus constructed and arranged in accordance with the principle of the invention, the apparatus includes a case having a first end closed by a first end cap formed with a catch from which the apparatus can be supported in a chosen environment, and a second end closed by a second end cap connected sealably and removably to the case.
Figure 2:
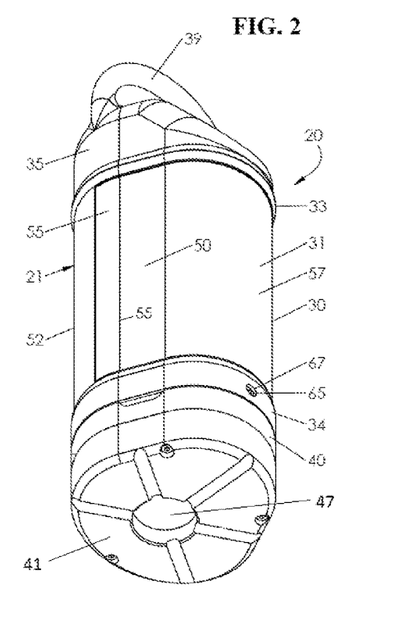
FIG. 2 is a bottom perspective view of the embodiment of FIG. 1.
Figure 3:
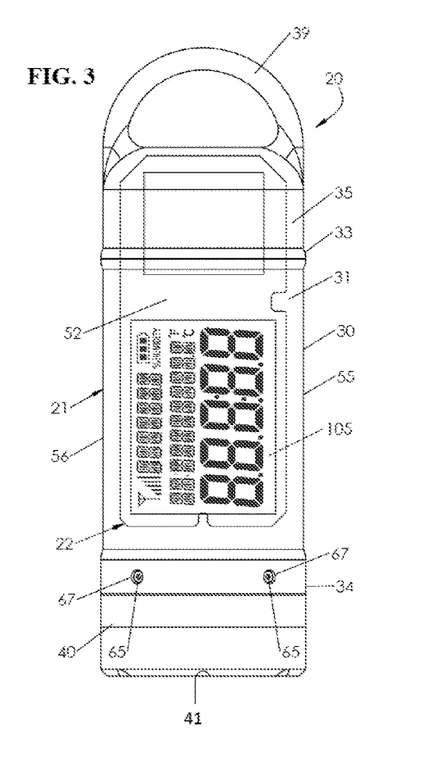
FIG. 3 is a front elevation view of the embodiment of FIG. 1.
Figure 4:
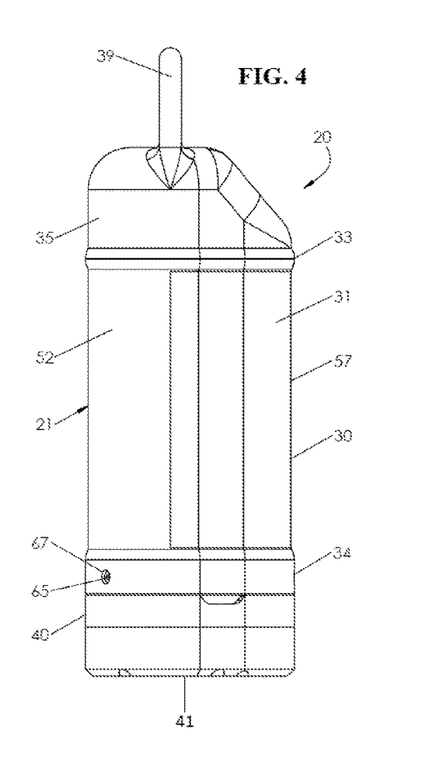
FIG. 4 is a right side elevation view of the embodiment of FIG. 1, the opposite left side elevation view being substantially the same thereof.
Figure 5:
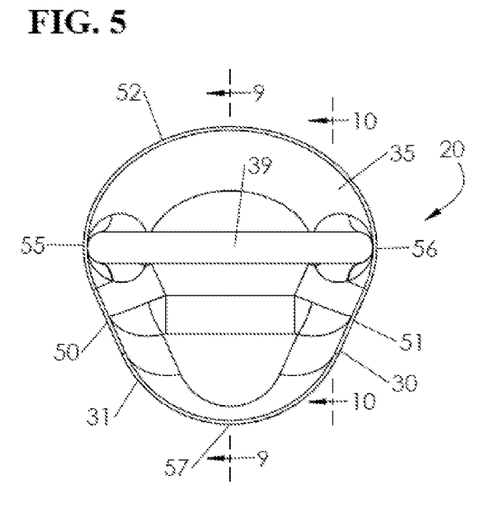
FIG. 5 is a top plan view of the embodiment of FIG. 1.
Figure 6:
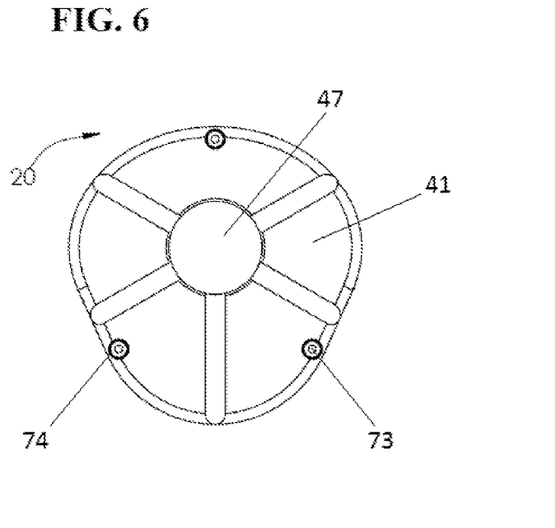
FIG. 6 is a bottom plan view of the embodiment of FIG. 1.
Figure 9:
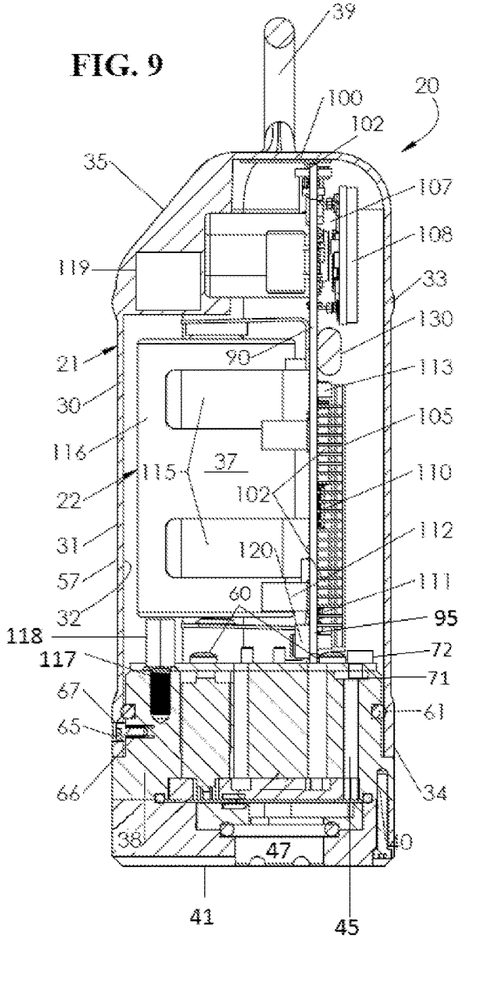
FIG. 9 is a section view taken along line 9-9 of FIG. 5.
Figure 10:
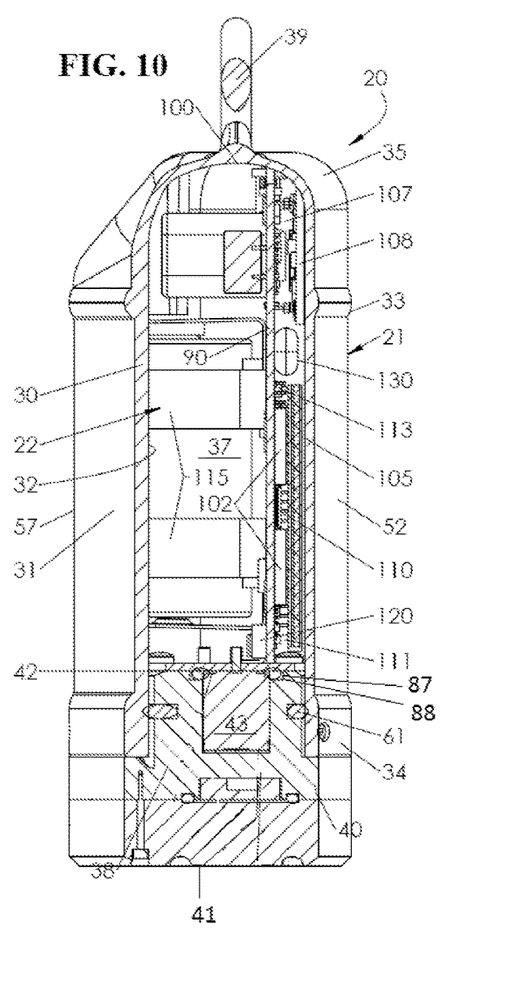
FIG. 10 is a section view taken along line 10-10 of FIG. 5.

Turning now to the drawings, in which like reference characters indicate corresponding elements throughout the several views, attention is directed to FIGS. 1-5, 9, and 10 illustrating a portable gas detecting and monitoring apparatus 20 including case 21, and gas detection and monitoring unit 22 mounted in case 21 in FIGS. 3, 9, and 10. Case 21 includes continuous sidewall 30 having outer surface 31 and inner surface 32, and opposed ends 33 and 34. End 33 is a first or upper end of case 21. End 34 is a second or lower end of case 21. Upper end 33 is closed by end cap 35. End cap 35, an upper end cap of case 21, is integral with upper end 33, being inseparable from upper end 33 of continuous sidewall 30 of case 21. End cap 35 cooperates with inner surface 32 of continuous sidewall 30 to form volume 37 in FIGS. 9 and 10 within which unit 22 is positioned. Lower end 34 encircles opening 38 to volume 37. Volume 37 is for receiving unit 22 placed therein through opening 38. Continuous sidewall 30 and upper end cap 33 are integrally moulded from a transparent plastic to enable the contents of volume 37 to be viewed therethrough for unit 22 inspection and for visually identifying therein moisture and other unwanted contaminants. End cap 35 is formed with a catch 39, a handle in the form of a half ring in this example, from which the apparatus can be supported/suspended in a chosen environment. Lower end 34 is closed by end cap 40. End cap 40, a lower end cap of case 21, is connected sealably and removably to continuous sidewall 30 for sealing and enclosing unit 22 in volume 37.

Continuous sidewall 30 is triangular, being a trilateral body, having three sides 50, 51, and 52, and three corners 55, 56, and 57, between upper end 33 and lower end 34. Preferably, sides 50, 51, and 52 and corners 55, 56, and 57 extend from upper end 33 to lower end 34. Sides 50 and 51 are straight and equal in length, side 52 is rounded (i.e. outwardly rounded), and each of the three corners is rounded (i.e. outwardly rounded), all of which defines the triangular shape of continuous sidewall 30, the trilateral body. Side 52 is a half ring or half pipe, in this example. The described shape of continuous sidewall 30, the trilateral body, is exceptionally strong, and extends to end cap 35.

Reference FIGS. 5, 7, and 8A and 8B in relevant part, end cap 40 is a multifaceted body, including outer end 41, inner end 42, inner base plate 83, and alternating plate 89.

Figure 7:
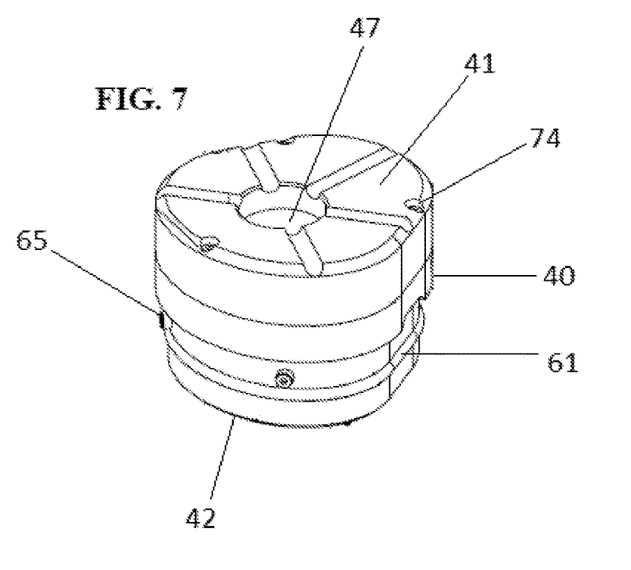
FIG. 7 is a bottom perspective view of the second end cap constructed and arranged in accordance with the principals of the invention.
Figure 8A:
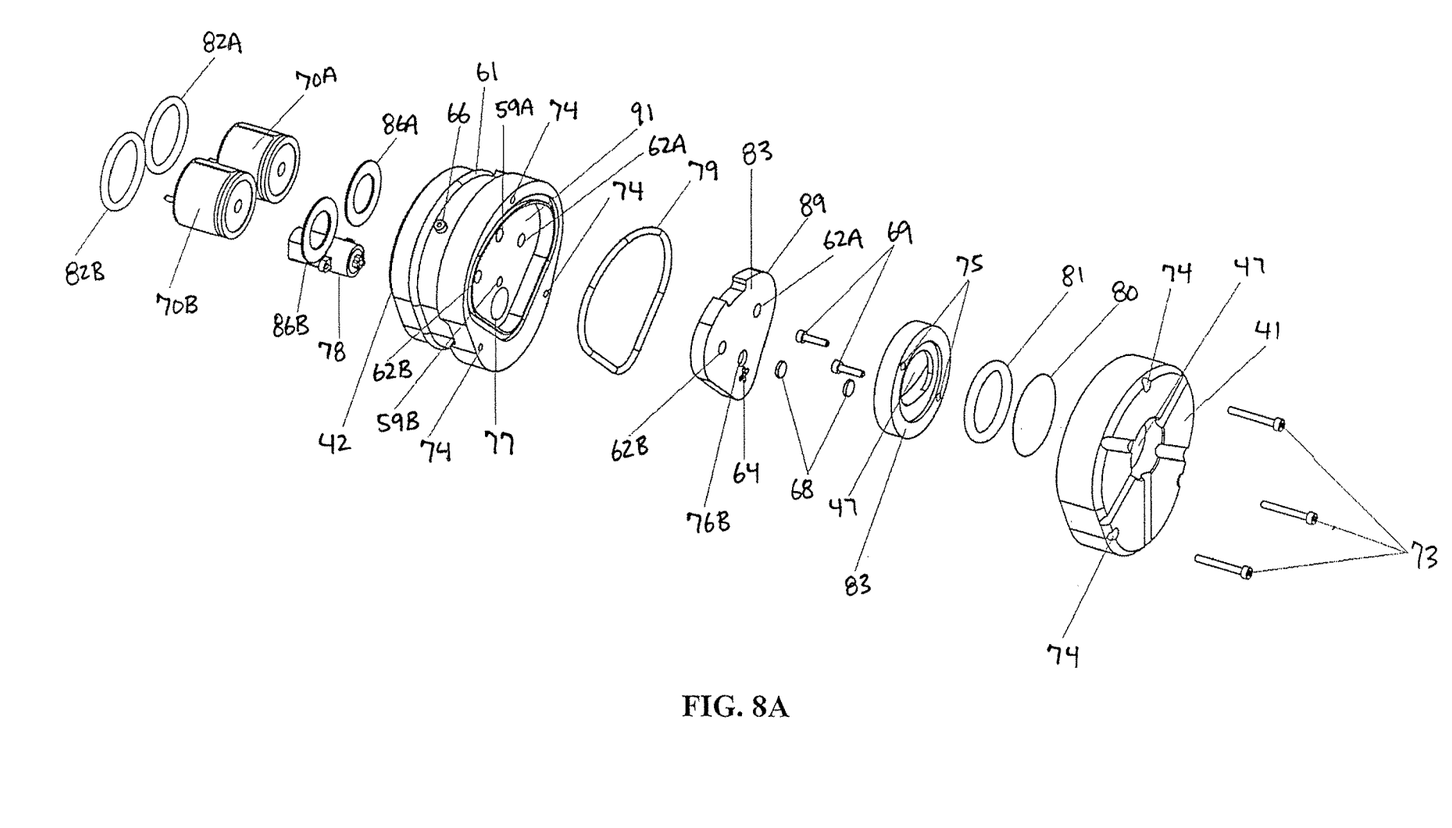
FIGS. 8A & 8B is are expanded views of the embodiment of FIG. 7, illustrating external base plate, set screws, attachment screws, filters, O-rings, inner base plate, alternating plate, magnets, alternating motor, and gas sensors; as they would appear withdrawn from the second end cap for illustrative purposes.
Figure 8B:
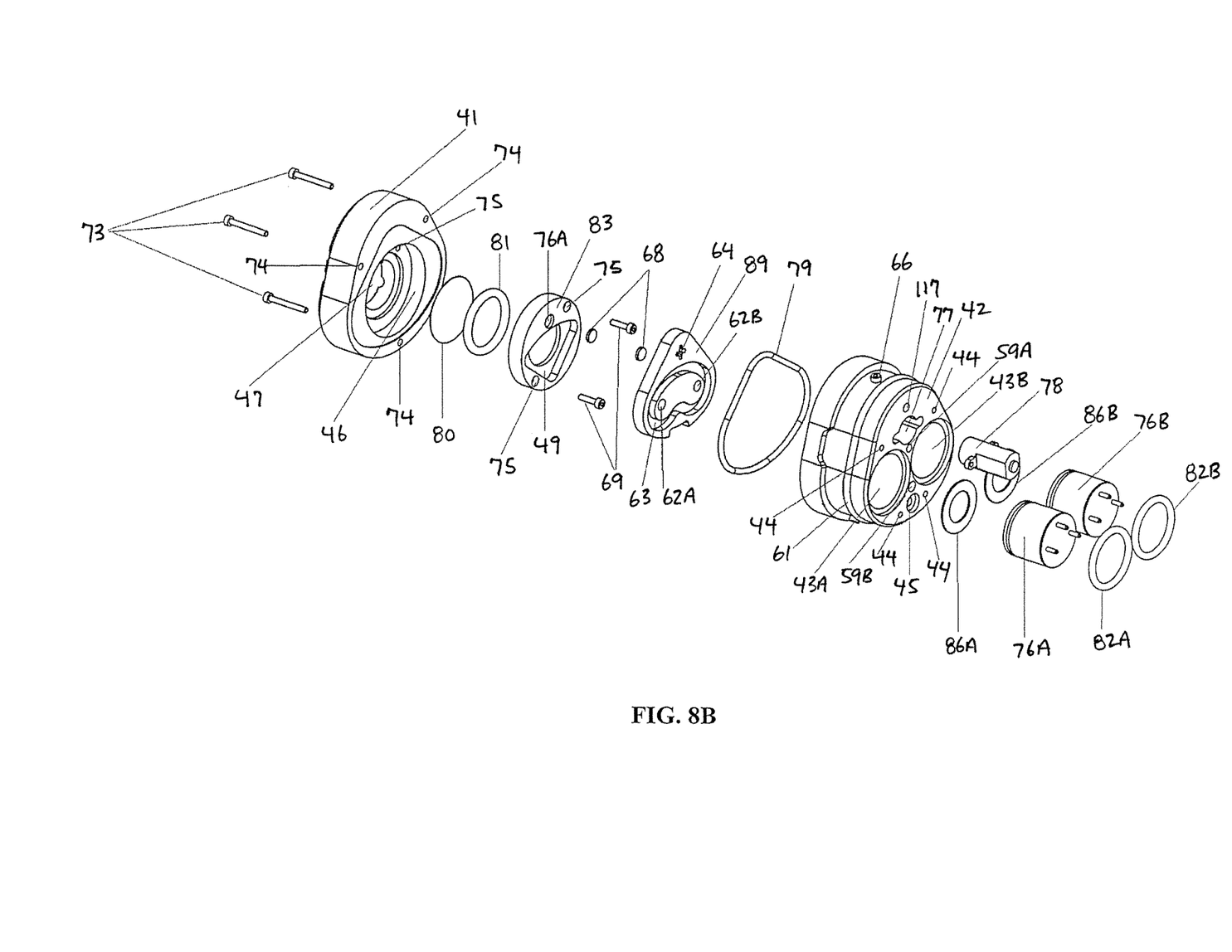

Outer end 41 incorporates a recess 46, a gas permeable filter 80, and O-ring 81, sealing the inner base plate 83 from the external environment. The inner base plate 83 is fastened into recess 46 by base fastening screws 69 trough outer base screw fastening holes 75.

Inner base plate 83 contains an environment flow recess 49, magnet recess 76A, and outer base screw fastening holes 75.

Alternating plate 89 on the face towards the inner base plate 83 contains, magnet recess 76B, to be in repelling contact with the inner base plate 83 magnetic recess 76A. Magnets 68 are placed in magnet recesses 76A and 76B, magnets 68 are to be in repelling force. The opposite side of the alternating plate 89, facing the inner end 42, contains a flow recess loop 63, which is in fluid contact with the inner volume 37. The environment flow recess 49 on the inner base plate 83, is in intermittent fluid contact with the gas sensors 70A and 70B via recesses 62A and 62B. O-ring 79 seals around the alternating plate 89 into recess 91 on the inner end 42, to seal from the ambient environment.

Inner cap end 42 is moulded sensor housing, consisting of; recesses 43A and 43B for housing of gas sensors 70A and 70B, recess 77 for alternating plate motor 78 to be inserted in, two environment flow holes 59A and 59B on the central axis are in fluid connection with the alternating plate flow recess loop 63 and the inner volume 37, temperature and humidity sensor passage 45 in fluid contact with the external environment via the coaxial passage 47, base mounting screw holes 66, threaded screw hole 117, and battery standoff 118 to be screwed in threaded screw hole 117. The alternating plate motor 78 shaft extends into recess 64 on the alternating plate 89.

Outer end cap 41 is fastened to inner base cap 42 by base fastening screws 73, via threaded fastening screw holes 74 first through outer end cap 41 then through threaded fastening screw holes 74 on inner base cap 42.

Referring to FIGS. 9 and 10, end cap 40 is inserted into inner end 42, first into opening 38 of lower end 34 and sealably encloses opening 38 to inner volume 37 for sealably enclosing inner volume 37 that accommodates unit 22 thereby sealing enclosing unit 22 in inner volume 37. Threaded holes 44 accept screws 60 that secure end cap 40 to unit 22. An O-ring 61, a gasket, provided in a groove in end cap 40 seals inner surface 32 of continuous sidewall 30, preventing gas and moisture ingress into inner volume 37. End cap 40 is secured in place with set screws 65 in FIGS. 1-4, which thread into corresponding threaded holes 66 (FIGS. 8A, 8B and 9) in the side of end cap 40 through corresponding through holes 67 (FIGS. 1-4 and 9) through continuous sidewall 30 near lower end 34, sealing unit 22 in inner volume 37.

Unit 22 sealed in inner volume 37 of case 21 includes a variety of sensors, including gas sensor 70A and gas sensor 70B, temperature and humidity sensor 71, and inner humidity and temperature sensor 72. Gas sensor 70A is sealed in recess 43A in end cap 40 in sealed fluid communication with an ambient atmosphere outside case 21 via passage 47, Gas sensor 70B is sealed in recess 43B in end cap 40 in sealed fluid communication with an ambient atmosphere outside case 21 via passage 47. Gas permeable membrane 80, a filter, used to prevent the ingress of large particles into recess 46, and on flowing recesses while at the same time enabling gas & moisture ingress to gas sensors 70A and 70B in recesses 43A and 43B, the gas permeable membrane 80 is sealed in place by O-ring 81. Gas sensors 70A and 70B are sealed into recesses 43A and 43B, by O-rings 82A and 82B, gaskets 86A and 86B. Gas sensor 70A has gasket 86A sealing it in recess 43A and is in fluid contact with the external environment, O-ring 82A seals behind gas sensor 70A and prevents gas and moisture ingress into volume 37. Gas sensor 70B follows the same as gas sensor 70B, gas sensor 70B has gasket 86B sealing it in recess 43B and is in fluid contact with the external environment, O-ring 82B seals behind gas sensor 70B and prevents gas and moisture ingress into volume 37.

Temperature and humidity sensor 71 is sealed in a counterbore of passage 45 at inner end 42 of end cap 40 in sealed fluid communication with an ambient atmosphere outside case 21 via passage 45. Non-gas permeable membrane 87, a filter, is sealed in place by O-ring 88. O-ring 88 prevents gas and moisture ingress into volume 37. An identical temperature and humidity sensor, inner humidity sensor 72 is in fluid contact with inner volume 37 and sealed from the external environment.

Unit 22 incorporates a printed circuit board ("PCB") assembly, including PCB 90 and sensor PCB 95, which carries, and electrically connects, the various components of unit 22. PCB 90 carries, and is electrically connected, to touch switch 100, externally operable reed switch 102 that acts as a secondary control, two additional externally operable reed switches, that act as additional controls, underneath an information display 105, a liquid crystal display ("LCD") in this example, that confronts, and that is visible through, side 52 of continuous sidewall 30, communication device 107 and universal communication socket 108, data processor 110, inertial sensor 111, data storage device 112, and calibration unit 113. Battery holder 115 connected to the back side of PCB 90 holds a battery 116, a dry cell battery pack in this example, that powers unit 22. When battery 116 is depleted, it may be removed from battery holder 115 and replaced with a fresh battery. Mounts 120 connect an end of sensor PCB 95 to an end of PCB 90. Sensor PCB 95 is horizontal, and PCB 90 extends vertically upright from one end of sensor PCB 95. Gas sensors 70A and 70B, temperature and humidity sensor 71, and inner temperature and humidity sensor 72 are carried by, and electrically connected to, sensor PCB 95, which is electrically connected to PCB 90. PCB 90 and sensor PCB 95 operatively connect data processor 110 to gas sensors 70A and 70B, temperature and humidity sensor 71, inner temperature and humidity sensor 72, inertial sensor 111, data storage device 112, display 105, calibration unit 113, and alternating plate motor 78, all of which work in concert with one another.

Alternating motor 78 activates and shifts alternating plate 89 thereby adjusting the accessible flow between sensors 70A and 70B, as the result of a prearranged event occurring by a preprogrammed function of the unit 22, via data processor 110.

Calibration unit 113 is operatively connected to data processor 110 for calibrating data processor 110 to a predetermined gas concentration measured by gas sensors 70A and 70B, and for zeroing gas concentration levels in relation to humidity levels sensed by inner temperature and humidity sensor 71. Calibration unit 113 is in fluid contact with the Inner volume 37. The Inner volume is consistently being conditioned by humidity control pack 130, and by the internal environmental filter 119. Inner volume 37, equalises and regulates gas sensors 70A and 70B, when they are respectively exposed to inner volume 37, to help prevent sensor leakages. Touch switch 100 is externally operable for selectively connecting data processor 110 to data storage device 112 to allow transfer of data from data storage device 112 to data processor 110. Communication device 107 is operatively connected to at least one of data processor 110 and data storage device 112, and preferably both, for enabling data transfer between an external destination and at least one of data processor 110 and data storage device 112. Communication device 107 is a conventional wireless communication device for enabling wireless data transfer between the external destination and at least one of data processor 110 and data storage 112. Communication device 107 employs one or more wireless communication protocols, such as radio frequency, Wi-Fi, and/or one or more other chosen wireless communication protocols. Inertial sensor 111 is sealed in volume 37 from the ambient atmosphere. A humidity control pack 130, inner temperature and humidity sensor 72, in volume 37 of case 21, is for measuring, temperatures and moisture in volume 37 of case 21. Apparatus 20 can be repaired or serviced, when inner temperature and humidity sensor 72 measures a predetermined level, and data processor 110 sends a signal, indicating excessive moisture in volume 37. Service or repair can be performed simply by detaching lower end cap 40 from continuous sidewall 30 and withdrawing lower end cap 40 and unit 22 from volume 37 to enable the skilled worker to carry out necessary repairs and/or maintenance. In this example, humidity control pack 130 is carried by PCB 90, and is visible through side 52.

Unit 22 is assembled by connecting PCB 90 and sensor PCB 95, each equipped with the corresponding unit 22 components, with mounts 120 and connecting inner end 42 of end cap 40 to sensor PCB 95 via screws 60, advancing unit 22 into volume 37 through opening 38 and releasably connecting end cap 40 to continuous sidewall with set screws 65 for sealably and releasably/removably connecting end cap 40 to continuous sidewall 30, closing and sealing opening 38 and volume 37 sealably enclosing unit 22 in volume 37 of case 21. When volume 37 is sealed by end cap 40, apparatus 20 is assembled. Sensor PCB 95 in volume 37 is connected to inner end 42 of end cap 40, and PCB 90 extends upright from sensor PCB 95 to exteriorly operable touch switch 100 at the top of end cap 35 where touch switch 100 is operated exteriorly. Inner end 42 of cap is shaped to correspond to the triangular shape of opening 38 of lower end 34 of case 21. Unit 22 in volume 37 is sufficiently spaced apart from the inner surfaces of case 21 for preventing unwanted contact between unit 22 and the inner surfaces of case 21.

Apparatus 20 is portable, in that it is easily taken up by hand and carried about for installation in a selected environment. Apparatus 20 is installed in an environment in which a particular gas is to be detected and monitored by securing apparatus 20 to selected location by suspending or supporting apparatus 20 in the chosen environment from catch 39. Apparatus 20 is switched on exteriorly, and operated exteriorly by, touch switch 100 and operates according to instructions pre-programmed into data processor 110, and operates with the ambient environment without the use of external controls. Touch switch 100 is conventional, is enclosed in volume 37 adjacent to end cap 35 opposite to catch 39, and is operated exteriorly by touching the outer surface of end cap 35 opposite to touch switch 100, requiring no physical contact with touch switch 100. The other switches of unit 22 are similarly exteriorly operable. Gas sensors 70A and 70B, temperature and humidity sensor 71, are in contact with the ambient environment and concurrently detect and monitor, in real time, gas, temperature and humidity uptake, respectively, of the ambient environment. Real time monitoring of humidity level via temperature and humidity sensor 71 and inner temperature and humidity sensor 72, helps prevents gas sensor 70A and 70B leakage when data processor 100 calculates humidity uptake of gas sensor 70A and 70B, and allows the skilled worker to take necessary action. Inertial sensor 111, in turn, and concurrently with the other sensors, senses, in real time, accelerations and movements that can occur if apparatus 20 is moved. Data processor 110 operatively coupled to the various sensors records and stores the data from the various sensors in data storage device 112, and displays the data on display 105 viewable through side 52. Display 105 is large, enabling it to display all of the sensor data and calculations made by data processor 110. Communication device 107 operatively connected to at least one of data processor 110 and data storage device 112, and preferably both, enables transfer of the data between an external destination and at least one of data processor 110 and data storage device 112. Communication device 107 is a conventional wireless communication device in a preferred embodiment for enabling wireless data transfer between the external destination and at least one of data processor 110 and data storage 112. Calibration unit 113 operatively connected to data processor 110 and gas sensors 70A and 70B, calibrates gas sensors 70A and/or 70B to a prearranged level to be measured from gas sensors 70A and/or 70B. Unit 22 can incorporate an alarm, such as an audible and/or visual alarm, operatively connected to data processor 110 and set to issue an audible and/or visual alarm when a concentration of gas being measured by gas sensors 70A and/or 70B reaches a predetermined level, when unit 22 is calibrated, and when unit 22 is set to predetermined settings. In a particular embodiment, data processor 110 transmits a signal wirelessly to an external destination when a concentration of gas being measured by gas sensors 70A and/or 70B reaches a predetermined level to alert a skilled worker that the concentration of gas being measured has reached a predetermined level.

As described above, gas sensors 70A and 70B, temperature and humidity sensor 71, and internal humidity sensor 72 are in contact with the respective ambient environments and concurrently detect and monitor, in real time the external environments, gas, temperature and humidity, and inner volume 37 humidity and temperature, respectively, of the ambient environment. During operation of unit 22, data processor 110 calculates the moisture uptake, i.e. humidity, uptake level and moisture uptake rate of the gas sensors 70A and 70B, and displays the calculated moisture uptake level and rate on display 105, in response enabling the skilled worker to extrapolate how long to deploy apparatus 20 at the chosen environment, when temperature and humidity sensor 71 is sensing moisture, i.e., humidity/moisture uptake level and humidity/moisture uptake rate, of the ambient atmosphere outside case 21. Furthermore, the calculated uptake level of gas sensors 70A and 70B enables the skilled worker to extrapolate the length of time needed before service of the apparatus 20 and gas sensors 70A and 70B in a chosen controlled environment; and time before apparatus 20 can be re-deployed. Unit 22 can incorporate an alarm, such as an audible and/or visual alarm, operatively connected to data processor 110 and set to issue an audible and/or visual alarm when the moisture uptake level measured by inner temperature and humidity sensor 72 reaches a predetermined level, and/or when the moisture uptake rate measured by inner temperature and humidity sensor 72 reaches a predetermined rate, to enable the skilled worker to remove apparatus 20 from the chosen environment for service and regenerating gas sensor 70A and 70B from moisture uptake and sensor decay. In a particular embodiment, data processor 110 transmits a signal wirelessly to an external destination when the moisture uptake level measured by inner temperature and humidity sensor 72 reaches a predetermined level, and/or when the moisture uptake rate measured by temperature and humidity sensor 72 reaches a predetermined rate, to enable the skilled worker to remove apparatus 20 from the chosen environment for service and regenerating gas sensors 70A and 70B and for preventing the gas sensors 70A and 70B from filling up and leaking in real time.

The present invention is described above with reference to illustrative embodiments. However, those skilled in the art will recognize that changes and modifications may be made in the described embodiments without departing from the nature and scope of the present invention. Various further changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A long term portable gas detecting and monitoring apparatus, comprising:
    a case, the case includes a continuous sidewall having opposed first and second ends, the first end is closed by a first end cap, the second end is closed by a second end cap, and the second end cap is connected sealably and removably to the continuous sidewall;
    a long-term gas detection and monitoring unit mounted in the case, the long-term gas detection and monitoring unit includes:
        gas sensors in sealed alterable fluid communication with an ambient atmosphere outside the case;
        an outer temperature and humidity sensor in sealed fluid communication with the ambient atmosphere outside the case;
        an inner temperature and humidity sensor in sealed fluid communication with the inner atmosphere of the case;
        a data processor operatively connected to the gas sensors, the outer temperature and humidity sensor, and the inner temperature and humidity sensor;
        data storage and an information display operatively connected to the data processor;
        a calibration unit operatively connected to the data processor for calibrating the data processor to a predetermined gas concentration measured by the gas sensor;
        an externally operable switch for selectively connecting the data processor to the data storage to allow transfer of data from the data storage to the data processor;
        a communication device connected to at least one of the data processor and the data storage for enabling data transfer between an external destination and at least one of the data processor and the data storage;
        a power supply mounted in the case, the power supply being operatively connected to power the long-term gas detecting and monitoring apparatus;
        an alternating plate or chamber, where the flow of fluids can be manipulated and/or redirected via passages to the gas sensors;
        an internal humidity regulator, wherein the humidity within the inner volume of the apparatus can be manipulated; and
        an internal environmental filter, wherein the internal volume can be filtered to remove unwanted matter.

2. The long term portable gas detecting and monitoring apparatus according to claim 1, wherein the gas sensors are mounted to the second end cap and are in sealed fluid communication with a first passage of the second end cap.

3. The long term portable gas detecting and monitoring apparatus according to claim 2, wherein the outer temperature and humidity sensor is mounted to the second end cap and is in sealed fluid communication with a second passage of the second end cap.

4. The long term portable gas detecting and monitoring apparatus according to claim 3, wherein the first passage, the second passage, and the passages to the gas sensors are separate from each other.

5. The long term portable gas detecting and monitoring apparatus according to claim 1, wherein the gas sensors are alterable to be in fluid connection with the inner volume, or ambient environment.

6. The long term portable gas detecting and monitoring apparatus according to claim 5, wherein the inner temperature and humidity sensor is mounted to the second end cap and is in sealed fluid communication with the inner volume.

7. The long term portable gas detecting and monitoring apparatus according to claim 1, wherein the information display confronts a rounded side of the continuous sidewall, the rounded side of the continuous sidewall being transparent to enable the viewing of the information display therethrough.

8. The long term portable gas detecting and monitoring apparatus according to claim 1, further comprising a catch formed in the first end cap from which the apparatus can be suspended.

9. The long term portable gas detecting and monitoring apparatus according to claim 1, wherein the communication device is a wireless communication device for enabling wireless data transfer between the external destination and at least one of the data processor and the data storage.

10. The long term portable gas detecting and monitoring apparatus according to claim 1, wherein the gas detecting and monitoring unit further includes an inertial sensor sealed from the ambient atmosphere, and the data processor is operatively connected to the inertial sensor.

11. The long term portable gas detecting and monitoring apparatus according to claim 1, wherein the first end cap is integral with, being inseparable from, the first end of the continuous sidewall.

12. The long term portable gas detecting and monitoring apparatus according to claim 1, wherein the data processor is for calculating at least one of moisture uptake level and moisture uptake rate of the gas sensors, when the outer temperature and humidity sensor is sensing moisture of the ambient atmosphere outside the case.

13. The long term portable gas detecting and monitoring apparatus according to claim 1, where in the communication device can be activated either operatively, or upon a pre-programmed function having been met, and the data processor sending a signal to activate the communication device.

14. The long term portable gas detecting and monitoring apparatus according to claim 1, where in the communication device is operatively connected to at least one of the data processor and the data storage for enabling data transfer between an external destination and at least one of the data processor and the data storage.

15. The long term portable gas detecting and monitoring apparatus according to claim 1, where in the communication device is activated upon a pre-programmed function being met, and the data processor sending a signal to the communication device to connect to at least one of the data processor and the data storage for enabling data transfer between an external destination and at least one of the data processor and the data storage.

16. The long term portable gas detecting and monitoring apparatus according to claim 1, wherein the gas sensors are the same, or different.

17. The long term portable gas detecting and monitoring apparatus according to claim 1, wherein the data processor is configured to send a signal to an alternating plate motor operatively connected to the alternating plate to perform a pre-programmed function for adjusting the alternating plate for manipulating and/or adjusting the flow of fluids via the passages to the gas sensors, upon a pre-programmed goal, result, or function having been achieved.

18. The long term portable gas detecting and monitoring apparatus according to claim 17, wherein the alternating plate motor is alterable between two or more positions, upon a certain preprogrammed goal, result or function having been achieved.

19. The long term portable gas detecting and monitoring apparatus according to claim 1, wherein the internal humidity regulator is for manipulating the moisture within the inner volume, to regulate the humidity level within the inner volume of the long term portable gas detecting apparatus.

20. The long term portable gas detecting and monitoring apparatus according to claim 1, wherein the internal environmental filter is for removing one or more types of unwanted matter present within the inner volume.

21. The long term portable gas detecting and monitoring apparatus according to claim 1, wherein the calibration unit of the long term portable gas detecting apparatus can function with the internal environmental filter.

22. The long term portable gas detecting and monitoring apparatus according to claim 1, wherein the calibration unit of the long term portable gas detecting and monitoring apparatus, is used to calibrate one or more of the long term portable gas detecting and monitoring apparatus's gas sensors.

23. The long term portable gas detecting and monitoring apparatus according to claim 1, wherein one or more of the gas sensors are configured to detect one or more types of gas.

24. The long term portable gas detecting and monitoring apparatus according to claim 1, wherein one or more of the gas sensors are configured to detect and determine a concentration of one or more gases.

* * * * *